(12) United States Patent
Ottini

(10) Patent No.: US 8,632,528 B2
(45) Date of Patent: Jan. 21, 2014

(54) METHODS FOR NONABLATIVE PHOTOREJUVENATION

(76) Inventor: Jorge Fausto Ottini, Larrea (AR)

( * ) Notice: Subject to any disclaimer, the term of this patent is extended or adjusted under 35 U.S.C. 154(b) by 1226 days.

(21) Appl. No.: 12/422,846

(22) Filed: Apr. 13, 2009

(65) Prior Publication Data

US 2009/0259219 A1 Oct. 15, 2009

Related U.S. Application Data

(60) Provisional application No. 61/044,311, filed on Apr. 11, 2008.

(51) Int. Cl.
*A61B 18/18* (2006.01)
*A61N 5/06* (2006.01)

(52) U.S. Cl.
USPC .................................. 606/9; 607/88

(58) Field of Classification Search
USPC ............ 606/3, 9, 11, 12; 607/88, 89; 128/898
See application file for complete search history.

(56) References Cited

U.S. PATENT DOCUMENTS

| | | | |
|---|---|---|---|
| 6,120,497 A | 9/2000 | Anderson et al. | |
| 6,228,082 B1 | 5/2001 | Baker et al. | |
| 6,350,276 B1 | 2/2002 | Knowlton | |
| 6,413,255 B1 | 7/2002 | Stern | |
| 6,589,237 B2 | 7/2003 | Woloszko et al. | |
| 6,610,052 B2 * | 8/2003 | Furumoto | 606/9 |
| 6,620,497 B2 | 9/2003 | Smith et al. | |
| 6,632,220 B1 | 10/2003 | Eggers et al. | |
| 6,659,999 B1 | 12/2003 | Anderson et al. | |
| 6,706,035 B2 * | 3/2004 | Cense et al. | 606/9 |
| 6,746,444 B2 * | 6/2004 | Key | 606/9 |
| 6,749,624 B2 | 6/2004 | Knowlton | |
| 6,832,996 B2 | 12/2004 | Woloszko et al. | |
| 6,920,883 B2 | 7/2005 | Bessette et al. | |
| 7,083,611 B2 | 8/2006 | Lemchen | |
| 7,097,639 B1 | 8/2006 | Almeida | |
| 7,118,563 B2 | 10/2006 | Weckwerth et al. | |
| 7,135,033 B2 | 11/2006 | Altshuler et al. | |
| 7,204,832 B2 | 4/2007 | Altshuler et al. | |
| 2001/0026186 A1 | 10/2001 | Watanabe et al. | |
| 2001/0051802 A1 | 12/2001 | Woloszko et al. | |
| 2003/0040739 A1 * | 2/2003 | Koop | 606/9 |
| 2006/0095103 A1 | 5/2006 | Eggers et al. | |
| 2006/0282067 A1 * | 12/2006 | Koop et al. | 606/9 |
| 2007/0088408 A1 * | 4/2007 | Amornsiripanitch | 607/88 |
| 2007/0198003 A1 | 8/2007 | Domankevitz et al. | |
| 2007/0255355 A1 | 11/2007 | Altshuler et al. | |
| 2008/0082148 A1 * | 4/2008 | Bernstein | 607/88 |

* cited by examiner

*Primary Examiner* — Tuan V Nguyen
(74) *Attorney, Agent, or Firm* — Polster, Lieder, Woodruff & Lucchesi, LC

(57) ABSTRACT

Methods for treatment of photoaging signs and skin texture includes precooling a surface of the skin to be treated, applying a beam of radiation to the surface of the skin having a wavelength between about 515 nm to about 1200 nm and a fluence less than about 26 j/cm2. The beam includes two or more pulses have different wavelengths wherein each pulse has a pulse width and a duration of a pulse (i.e., pulse duration), and wherein the second pulse is superimposed on the first pulse over the same treatment area. Also, the method includes applying dynamic cooling to the surface of the skin simultaneous with applying the beam of radiation to the surface of the skin.

22 Claims, 10 Drawing Sheets

BROAD-BAND SPECTRUM WITH
LONG PASS (CUT OFF) FILTER

SPECTRAL RANGE: 515-1200 nm

QUANTUM HR-SR
FILTERS:

560 nm
640 nm
645 nm
695 nm

FIG. 8A
FIG. 8B
FIG. 8C
FIG. 8D
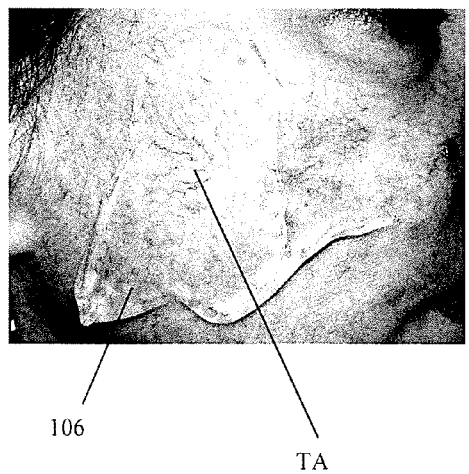
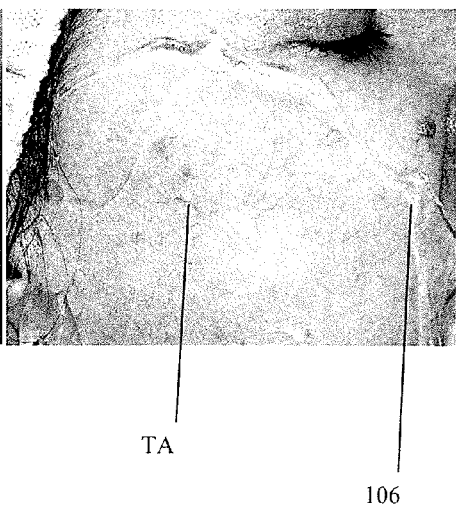

METHODS FOR NONABLATIVE PHOTOREJUVENATION

CROSS-REFERENCE TO RELATED APPLICATIONS

This application claims priority to U.S. Provisional Application No. 61/044,311 filed Apr. 11, 2008, the disclosure of which is incorporated herein by reference.

FIELD

The present disclosure relates to systems and methods for treating determatological conditions and, more specifically, to systems and methods for nonablative photorejuvenation of skin including tightening of the dermis and promoting production of new collagen.

BACKGROUND

The statements in this section merely provide background information related to the present disclosure and may not constitute prior art.

Non-ablative laser/light treatments, e.g., facial photo rejuvenation, are becoming an increasingly popular procedure in correcting the undesired side effects of photo and chronological aging. Non-ablative facial treatments have been shown to remove hair and improve rhytides, pilosebaceous changes, pigmentary skin alterations, lentigines, and vascular lesions including facial telangiectasias and diffuse redness. Such typically require minimal or no healing time and are convenient and less risky for a patient. Intense Pulsed Light (IPL) is widely known for the treatment of photoaging signs, vascular and pigment pathology, and skin texture. This includes vascular and pigmentary changes associated with photoaging, lentigens, telangiectasia and symptoms of rosacea.

SUMMARY

The inventor hereof has succeeded at conceiving a nonablative treatment of photorejuvenation for tightening of the dermis and/or promoting collagen production, among other benefits.

According to one aspect, a method for treatment of dermatological conditions of skin including precooling a surface of the skin, applying a beam of radiation to the surface of the skin having a wavelength between about 515 nm to about 1200 nm, and a fluence less than about 26 j/cm2. The beam includes at least one pulse and often two or more pulses each having a pulse width and a pulse duration and applying dynamic cooling to the surface of the skin simultaneous with applying the beam of radiation to the surface of the skin.

According to another aspect, a system for tightening of the skin having means for precooling a surface of the skin, means for applying a beam of radiation to the surface of the skin having a wavelength between about 515 nm to about 1200 nm and a fluence less than about 26 j/cm2. The beam includes at least two pulses with each pulse having a pulse width and a pulse duration, but which can include one being superimposed on the other immediately following the first. Also included is means for applying dynamic cooling to the surface of the skin simultaneous with the applying of the beam of radiation to the surface of the skin.

According to another aspect, a method for treatment of dermatological conditions of skin includes precooling a surface of the skin for a first treatment, applying a first beam of radiation to each of a plurality of treatment areas of the surface of the skin, the first beam having a wavelength between about 560 nm and a fluence less than about 26 j/cm2 and wherein the beam includes a first pulse and a second pulse applied to each treatment area, applying a first dynamic cooling to the surface of the skin simultaneous with applying the beam of radiation, precooling a surface of the skin for a second treatment, the second treatment following the first treatment by a predefined period of time exceeding one week, applying a second beam of radiation to each of the treatment areas, the second beam having a wavelength between about 590 nm and a fluence less than about 26 j/cm2 and wherein the beam includes a first pulse and a second pulse applied to each treatment area, and applying a second dynamic cooling to the surface of the skin simultaneous with applying the second beam of radiation. Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIGS. 8A-8D illustrates application of a precooling gel to a treatment area.

It should be understood that throughout the drawings, corresponding reference numerals indicate like or corresponding parts and features.

DETAILED DESCRIPTION

Figure 1:
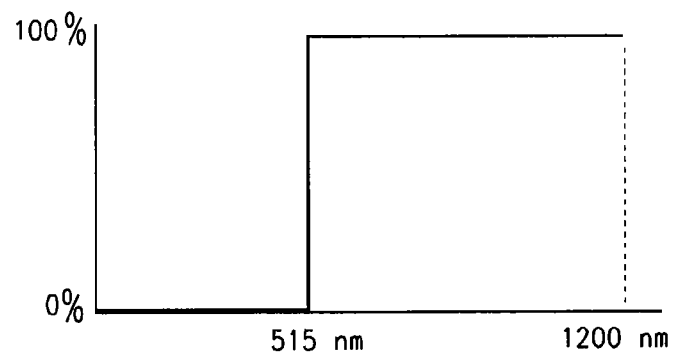
FIG. 1 is an illustration of the wavelengths between 515 nm and 1200 nm suitable for use with some embodiments as described herein and in particular the use of various filters.
Figure 1:
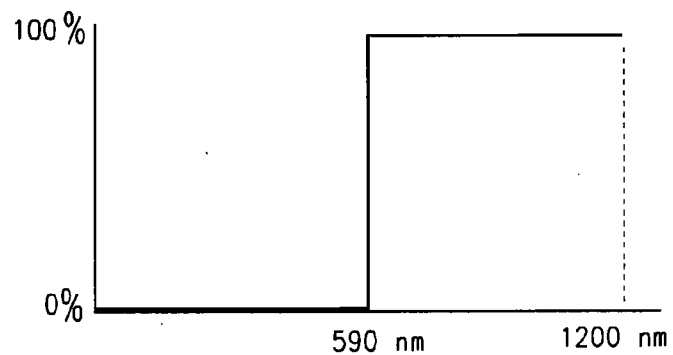

The following description is merely exemplary in nature and is not intended to limit the present disclosure or the disclosure's applications or uses.

Before turning to the figures and the various exemplary embodiments illustrated therein, a detailed overview of various embodiments and aspects is provided for purposes of breadth of scope, context, clarity, and completeness.

Photorejuvenation as utilized herein is the use of visible or infrared light energy sources to reverse the process of sun induced or environmental damage to the skin. Such nonablative rejuvenation as described herein provides for improved esthetic characteristics of photoaged skin, including the appearance of dyspigmentation, static, fine wrinkles, coarse texture, prominent pores, telangiectasias, and skin laxity. When the wavelength and the target meet (selective photothermolysis), the skin temperature rises. Photorejuvenation can be provided, for example, by the applying in different treatments two different wavelengths, one treatment at a wavelength between 500-590 to treat the Melanin tissue and a second treatment at a wavelength between 550-610 for treatment of vascular tissue. A typical Intense Pulsed Light (IPL) laser recommends power levels for such treatments from between 25 and 40 joules/cm$^2$ (or j/cm$^2$) and one such IPL laser specifically recommends that treatments be no less than 25 j/cm$^2$. The combination of Melanin absorption and oxyhemoglobin, along with the water absorption can produce a deep penetration of light in the superficial and deep layers of the skin, with heat accumulation and cell stimulation. In general, pigment and vascular improvements are more evident than the changes in skin texture and wrinkles. However, multiple treatments at a first wavelength followed by multiple treatments at a second wavelength have been shown to provide a gradual and progressive improvement to the tightness of the skin.

In some embodiments as described herein, contrary to the recommendation of manufacturers of IPL lasers and common practice for such use, the inventor hereof has found that improved treatment is provided when a lower energy dose is applied to the treatment area in multiple applications (such as 2 to 4 applications of the IPL laser) on the same spot. In this manner, and contrary to the IPL laser manufacturer instructions (wherein they instruct that power should not be below 25 j/cm$^2$, the epidermis can be heated to a higher temperature when a lower power level is used with repeated treatments as compared to a higher power setting that can be applied with a single application of a typically recommended IPL laser energy setting since such high power treatments must be limited in the number of applications at the same spot or treatment area in order to avoid damaging the skin. By using the lower energy level and applying it in multiple applications, the epidermis is heated while the general area of treatment is cooled thereby providing a tightening of the epidermis.

For example, one embodiment of photorejuvenation as described herein, utilizes a Quantum IPL using a lower energy level (such as 22 to 26 joules/cm$^2$ as compared to the 25 to 40 joules/cm$^2$ recommended by the manufacturer) but wherein the lower level energy applications are applied in repeated simultaneous applications to epidermis having an integrated skin cooling crystal that cools the epidermis to 40° C. during IPL treatments versus 65° C. without cooling (contact cooling or parallel cooling). The combination with the use of a precooling gel at −8 to +2° C. along with dynamic cooling simultaneous with the radiation treatment allows the dermis temperature to rise to a higher temperature for treatment even with the lower energy levels of between 22 and 26 joules/cm$^2$ with a repeated application of the IPL without causing an excessive undesirable rise in the temperature of the epidermis. When precooling and dynamic cooling are combined as described herein, safe and effective treatment of the skin tissue can be achieved.

Many substances, water, melanin, and hemoglobin are the target of the IPL as they diffuse heat within the structures with collagen, thus causing the remodeling by means of stimulus. An immediate post treatment edema of endothelial cells, connective tissue, with inflammatory cell emergence have been observed which are then followed by collagen and elastin formation over the ensuing weeks following treatment. Additionally, cytokine secretion and other growth factors that influence the collagen remodeling have also been observed following the above described method of treatment.

In another embodiment, a system and method for treatment of photoaging signs and skin texture includes precooling of a surface of the skin such as by application of a cooling agent; applying a beam of radiation to the surface of the skin having a wavelength between about 515 nm to about 1200 nm and a fluence less than about 26 j/cm2. The beam includes at least one pulse (and often multiple pulses at the lower energy level) with each having a pulse width and a pulse duration. Additionally, the method includes applying dynamic cooling to the surface of the skin simultaneous with application of the beam of radiation. In some embodiments, two or more pulses of different wavelength can be applied during a subsequent treatment.

In various embodiments, system and methods for treatment of dermatological conditions of skin include treatment of the neck, face, chest, hands and legs of a patient, by way of example, without being limited to such treated areas.

The described precooling a surface of the skin, can be preformed in any suitable manner. This can include precooling the surface of the skin by applying a cold contact gel or other form of cold compacts. Any cooling can be suitable but in some exemplary embodiments, a suitable cooling will apply a cooling temperature to the surface of the treatment area of between about −8° C. to about 2° C. or can be as high as 6° C. Generally, the precooling is performed immediately before applying the radiation beam.

Figure 2:
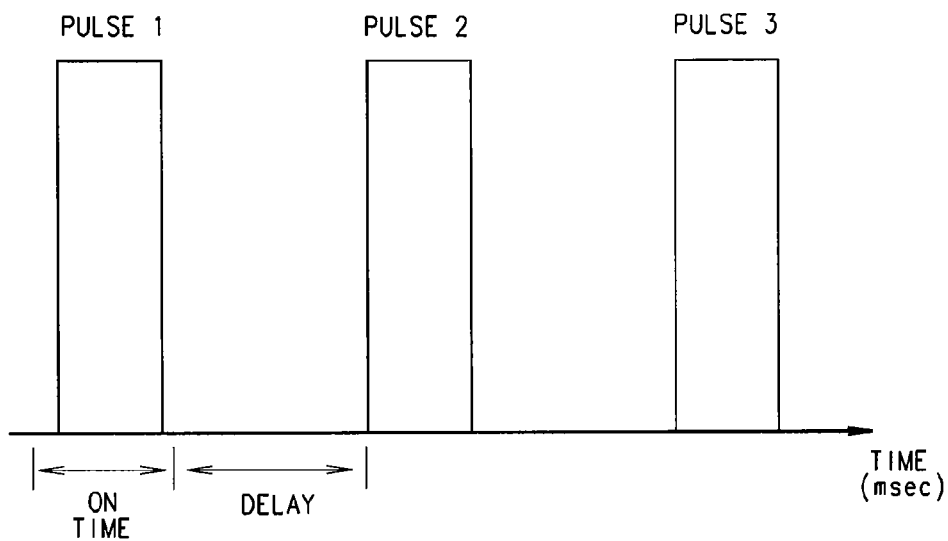
FIG. 2 is a time chart illustration of the IPL pulsing algorithm showing the adjustable pulse parameters according to some exemplary embodiments.

Applying a beam of radiation to the surface of the skin includes applying wavelengths between about 515 m to about 1200 nm, and having a power or fluence less than about 26 j/cm2. For example, as shown in FIG. 1, the wavelengths of each pulse can be between 515 nm and 1200 nm during a first or first set of treatments and can be between 590 nm and 1200 nm during a second or second set of treatments. As one example, a first set of 2 or 3 treatments is performed at about 560 nm, which is thereafter followed by one or two treatments at about 590 nm. Various filters can also be used such as a filter of 560 nm, 640 nm, 645 nm, and 695 nm as noted in FIG. 1 to obtain various combinations of wavelengths for the multiple treatments. The radiation beam can be any type of beam of suitable wavelength but in some embodiments has one or a plurality of pulses having a predetermined pulse width and predetermined pulse duration. Exemplary pulses are illustrated in FIG. 2 wherein each radiation pulse includes an "on time", with a defined delay between pulses. The radiation application parameters include pulse time, pulse delay, numbers of pulse applied in a single burst, and the fluence or power of each pulse. Such radiation beams can be configured as described herein to act on all photoaging signs, pigment and vascular disorders, and skin texture such that appropriate targets of melanin-hemoglobin-water provide for contracting and tightening of the skin.

As described above, employment of lower energy doses (subpurpuric for the vascular collapse) can be provided by multiple passes of a lower energy radiation beam in the wavelengths between 515 nm and 1200 nm. As described, while one device for generating the radiation beam is an Intense Pulsed Light (IPL), the present method of treatment is not limited to the IPL as the radiation source as it is not the only system capable of producing the radiation beam as other laser systems and radiofrequency sources are also possible and within the scope of the present disclosure.

Figure 3:
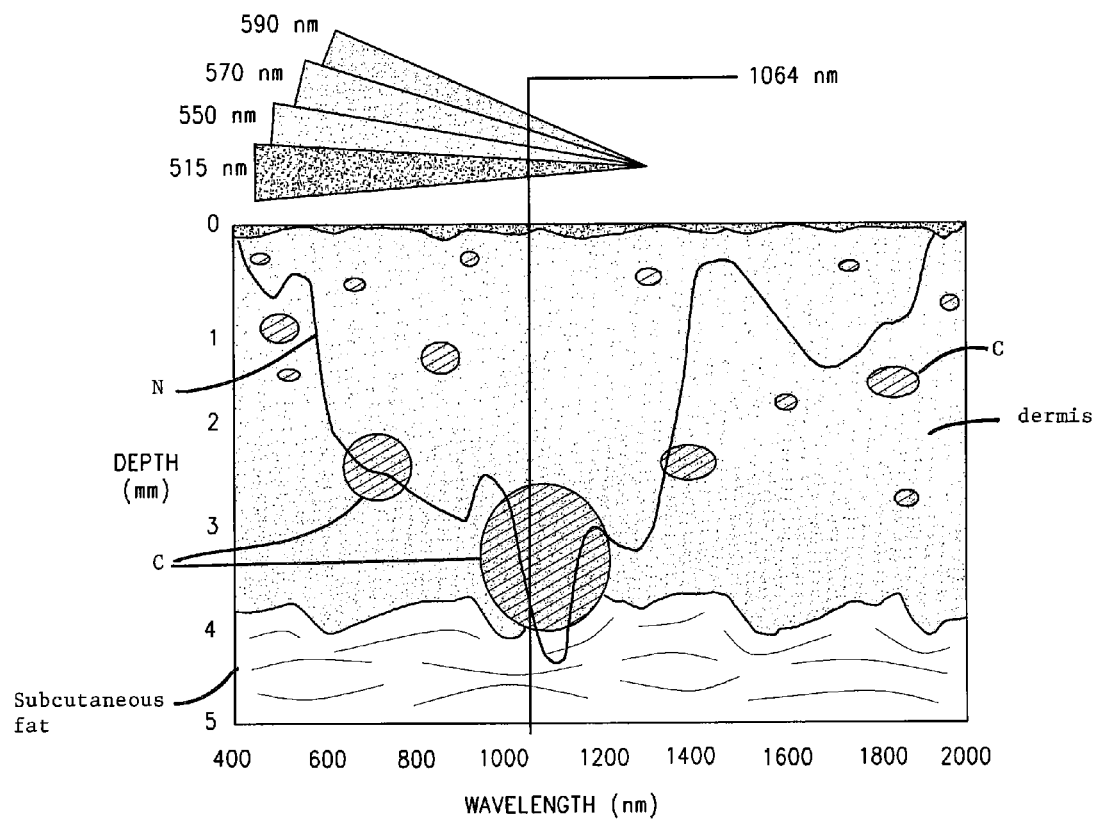
FIG. 3 is a chart illustrating the skin depth of photo rejuvenation as a function of wavelengths of light.

Selection of particular wavelengths is also provided in some embodiments. As shown in FIG. 3, the wavelength of the applied radiation for the treatments can be selected as a function of the desired depth within the dermis that is to be treated. As shown by the line N, the radiation penetrates the dermis and therefore can result in the treatment, such as by heating, of the dermis at a desired treatment depth. As shown, at 1064 nm, the treatment depth is nearly 4 mm which is close to the depth of the dermis. As such, if a particular portion of the dermis (as indicated by the circles C) are to be treated, the selection of the wavelength must be such as to be appropriate.

For various embodiments of the present methods, applying the radiation beam having a first band selected between about 500 nm to about 590 nm and subsequently applying in a second treatment a second radiation band between about 550 nm to about 660 nm (as segregated by the filters described above), has been found to have benefit of the present disclosed treatments in particular for treatments for skin tightening. As seen in FIG. 3, these wavelengths have primary affect on the dermis at a depth of less than 1 mm. As known in the art, bandwidth selection can be provided by filtering the radiation beam using one or more filters, such as cut off filter, by way of example. In some embodiments, two cut off filters can be utilized, one in each treatment, with one about 560 nm and the second about 590 nm. Such a selected spectrum was found by the inventor to address skin disorders and target the pigment (melanin, higher percentage in epidermis and basal layer) and vascular (hemoglobin, deeper vessels and dermis) components of the skin that heretofore were not considered treatable by such IPL lasers.

Additionally, the radiation spectrum can have a variety of different powers but as identified by the current inventor, it is desirable to maintain a relative low power for tightening of the dermis and for encouraging collagen production, among other benefits. In one embodiment, the section of the radiation beam has a power from 15 j/cm2 to 26 j/cm$^2$ with about 26 j/cm$^2$ being the maximum in many cases. In another case, the radiation beam power may be limited to between about 15 j/cm$^2$ and 25 j/cm$^2$. This is in contrast to the higher energy levels recommended by most IPL manufacturers of between 25 and 40 j/cm$^2$. However, in other embodiments, various other power levels are also desirable that can be above 26 j/cm$^2$ and possibly above 40 j/cm$^2$ if the pulse width and duration of the pulse are significantly reduced. In one embodiment applying the radiation beam having a power of between about 22 j/cm2 to about 30 j/cm2 was found to be effective if the pulse width and pulse duration are significantly reduced.

Where the radiation beam is generated in two or more pulses, the pulse can have a predefined pulse width and a predefined pulse delay or interval/spacing. Where 2 or 3 pulses are provided, the modification of the duration of each pulse and also the modification of interval between the pulses can be customized and can therefore provide numerous combinations that can be adapted to any treatment according to the pathology and skin type being treated. As addressed above, a second or third pulse can be superimposed on a first pulse following the first pulse in treatment of the same treatment area. In other applications, 2 to 4 pulses can be applied of the lower energy level IPL laser, with one particular method applying 3 simultaneous pulses to the same treatment area before relocating the IPL laser to the next treatment area. For example, in one exemplary embodiment the method can include applying two pulses of radiation, a first pulse is a 1 pulse having a duration of about 2.4 msec and a second pulse is a 2° pulse having a duration of about 5 msec to about 6 msec, each applied to the same treatment area. In some cases, the second pulse can be delayed from the first pulse by about 20 to about 50 msec and in other cases by about 30 to about 50 msec. In one exemplary embodiment, a 2.4 msec pulse, with a delay of 5.5 msec followed by a 6.0 msec pulse has been found to be highly successful. However, it has also been found that the length of the pulses can be varied by the applicant from between 2.4 msec to about 15 msec dependent on the skin tone. For example, this can be a first pulse of 2.4 msec, with a delay of 15 msec and a second pulse of 15 msec for lighter skin tones or 2.4 msec, a delay of 15.0 msec and a second pulse of 6.0 msec for darker skin tones. In such embodiments, a single treatment can include 250 to 400 pulses. The method can include multiple such treatments separated by 2 to 4 weeks each.

Figure 4:
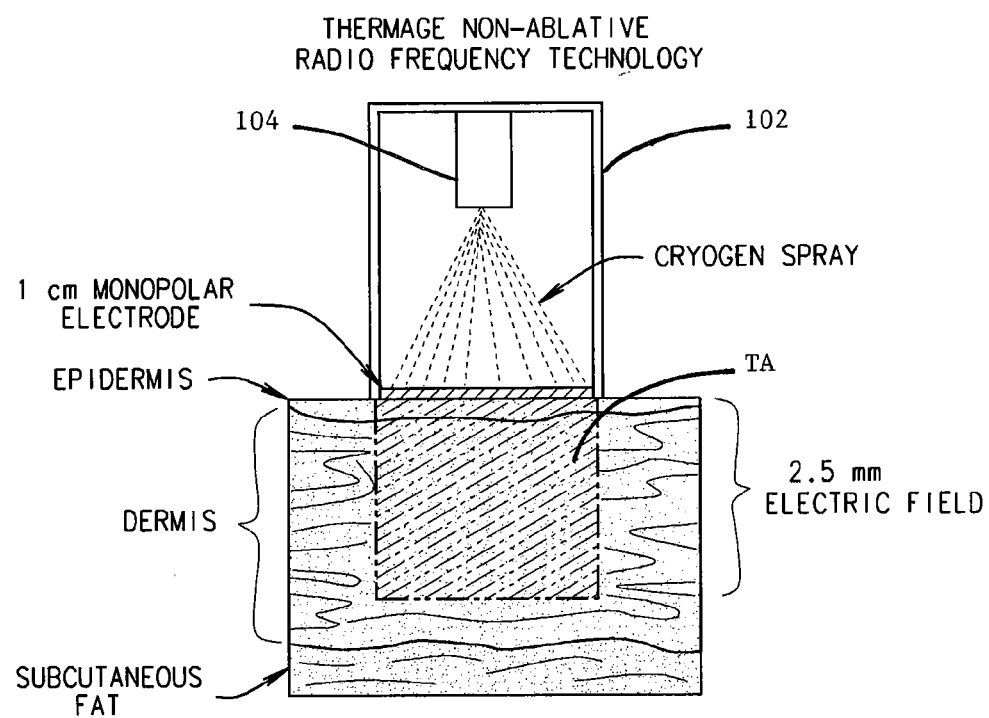
FIG. 4 is a chart illustrating the simultaneous dynamic cooling of the skin surface using a cryogen spray according to one exemplary embodiment.
Figure 5:
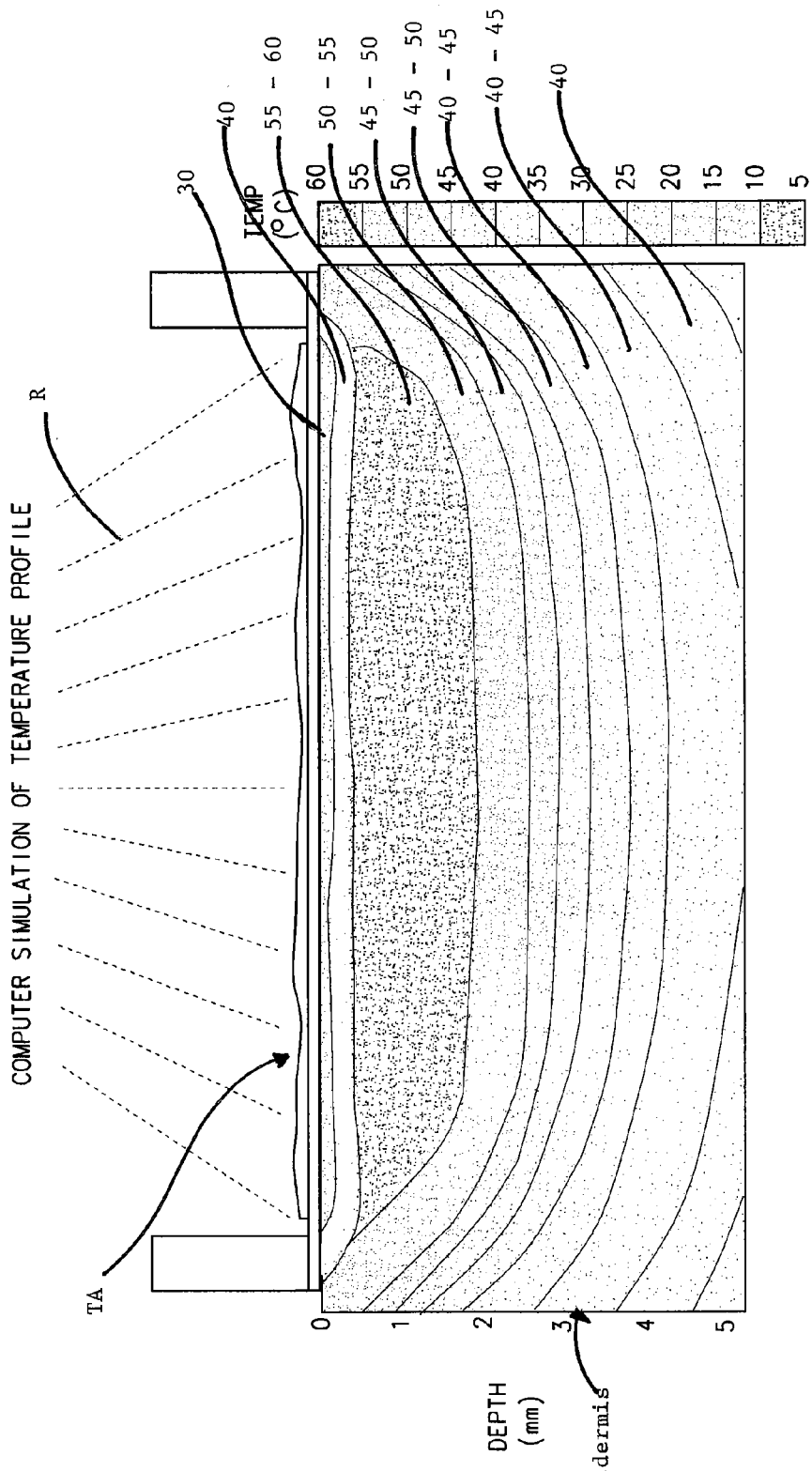
FIG. 5 is a computer simulation of the temperature profile for dynamic cooling according to one exemplary embodiment.

Dynamic cooling can be provided by application of a cooling spray or airflow during the treatment. In one embodiment, the dynamic cooling is provided by applying a cryogen spray (as shown in FIG. 4) to the surface of the skin immediately before and during the application of the radiation beam and possibly immediately thereafter for some period of time. As in FIG. 4, the cryogen spray, in this exemplary embodiment, is applied simultaneous with the thermage non-ablative radio frequency generated radiation beam within the 1 cm monopolar electrode 102. The spray is emitted by a jet 104 to the 1 cm treatment area TA of the epidermis. The radiation beam R (not shown in FIG. 4), is applied at a depth of 2.5 mm of the dermis also defined by the 1 cm treatment area of the electrode 102. Such dynamic cooling can be by any means where the cooling can be applied simultaneous such cooling occurs with the heating from the application of the radiation beam so as to cool the epidermis. The amount of dynamic cooling can also vary depending on the amount of precooling and the amount of heating applied by the radiation beam. In some exemplary embodiments, applying dynamic skin cooling includes cooling the skin by more than about 10° C. during applying the radiation beam or by cooling the surface of the skin to about 40° C. during application of the radiation beam.

Figure 6:
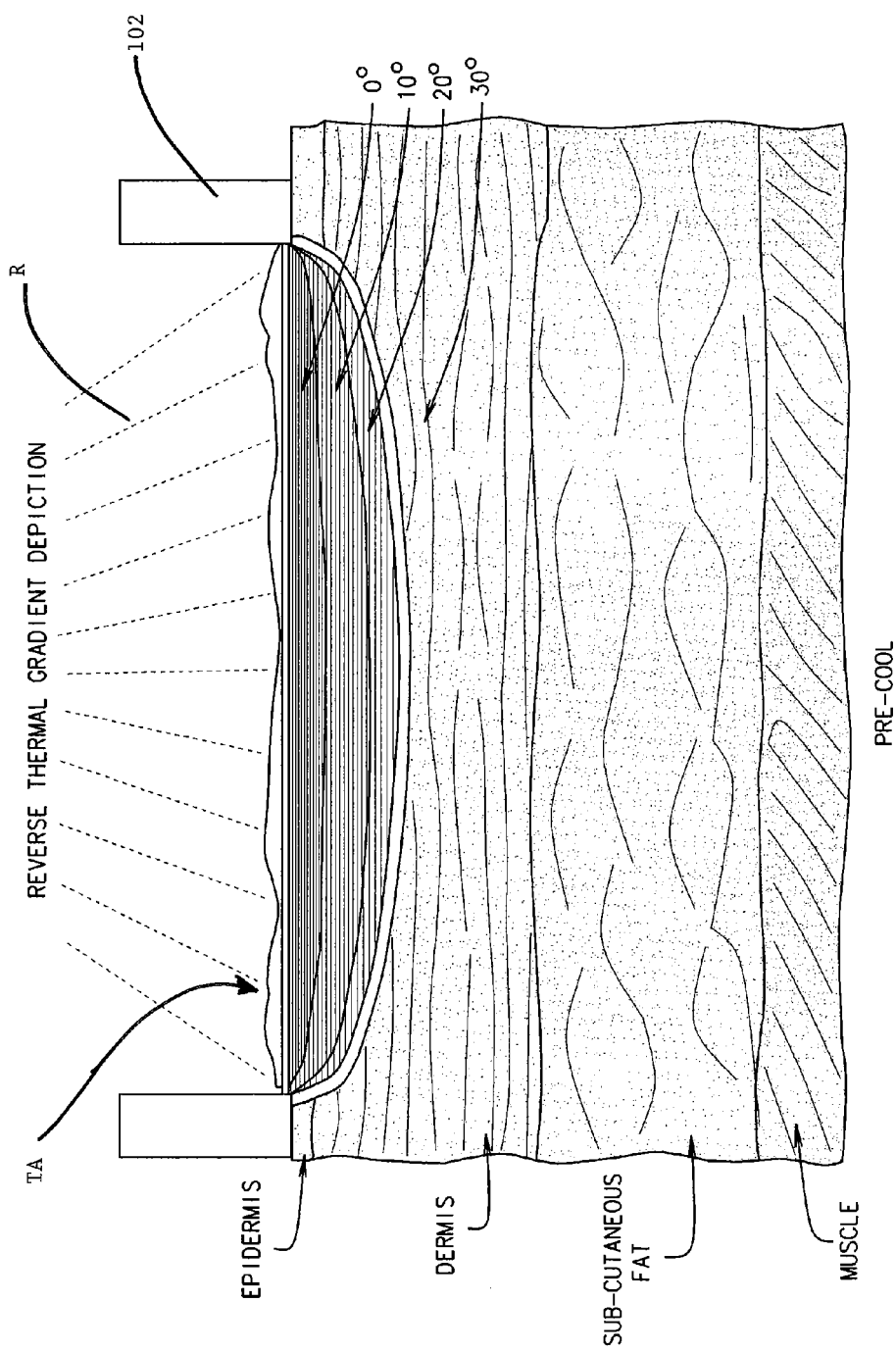
FIG. 6 is a profile view of human tissue being treated during treatment with pre-cooling but without simultaneous dynamic cooling.
Figure 7:
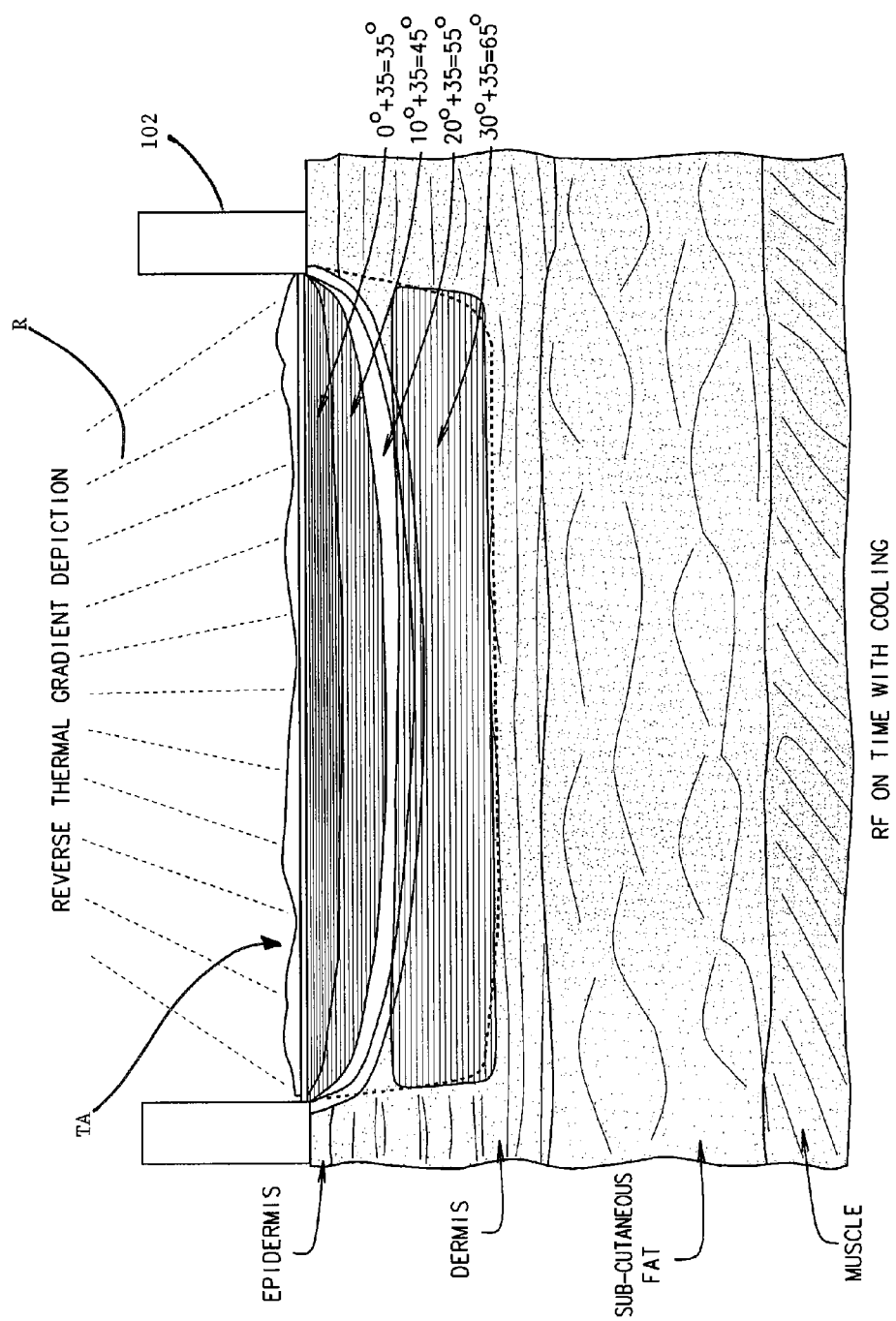
FIG. 7 is a profile view of the human tissue of FIG. 6 illustrating the effect of the simultaneous dynamic cooling during the application of a radiation beam during one exemplary embodiment of treatment.

The benefit of pre-cooling and simultaneous dynamic cooling is illustrated in FIGS. 6 and 7. FIG. 6 illustrates the application of pre-cooling to the treatment area TA wherein the temperature from the epidermis to the dermis ranges from 0° C. to 30° C. During treatment, the pre-cooled and dynamic cooled treatment area (as shown in FIG. 7) results in an increase of the temperature from the epidermis to the dermis ranges from 35 to 65° C., an average temperature increase of 35° C. As such, the pre-cooling and dynamic cooling of the treatment area has been determined to result in improved treatment of the skin for skin tightening.

Also as noted above, the use of lower power radiation has been found to be advantageous as described here as compared to other skin treatments. As such, multiple treatments of pre-cooling along with applying the lower power radiation beam and applying dynamic cooling, have been found by the present inventor to be effective in tightening of the dermis and promoting collagen production. For example, such multiple treatments can be provided at intervals of between about 3 and about 6 weeks. One, two, or more such treatments can be utilized and are within the scope of the present disclosure.

Dynamic cooling can be provided by an IPL-Quantum system. Generally, IPLs utilizing a xenon flash lamp are used to produce an electric glow discharge having extremely intense, incoherent, full-spectrum white light for very short durations. One or more cutoff filters can be used to filter the IPL discharge to provide the desired bandwidth and wavelengths. By way of examples, the use of cutoff filters enables the selection of different wavelengths, from 560 nm to 755 nm, and in some cases 560-590 nm filters. Through the use of such filters, IPL generated radiation beam can be filtered to produce a spectrum from 500 nm to 1200 nm. The IPL-Quantum includes a chiller on crystal-head and can apply a cryogen spray to the surface of the skin being treated.

In some embodiment of the present treatment, the inventor hereof has found that applying a post treatment moisturizing neutral cream to the surface of the treated skin can also be useful in promoting post treatment benefits. The neutral cream can be of any type of moisturizing cream and in one embodiment has a sun protection factor (SPF) from about 30 to about 60.

As provided herein, the lower levels of energy as described herein has been shown to have a direct impact on the fibroblasts and thereby produces more collagen than previously believed or available with higher levels of energy. After these treatments, the new collagen formation has been confirmed. This collagen remodeling has been found to continue for periods of 6 to 12 months.

Changes and improvements in patients are sometimes subjective. The photographic evaluation of patients, histological changes of neocollagen formation, is also difficult and does not always have a clinical correlate and vice versa. However, when skin contraction and tightening are produced, since the phenomenon is three-dimensional, it can be captured and documented by means of photographs.

The treatments as described herein can be used, for: 1) Jowls improvement, 2) Double chin improvement, 3) Jaw contour improvement, and 4) Eyebrows height, with improvement of the upper palpebral fold, by ways of example.

Figure 9A:
FIGS. 9A and 9B are before and after images of a patient treated according to one exemplary embodiment.
Figure 9B:
Figures 10A, 10B:
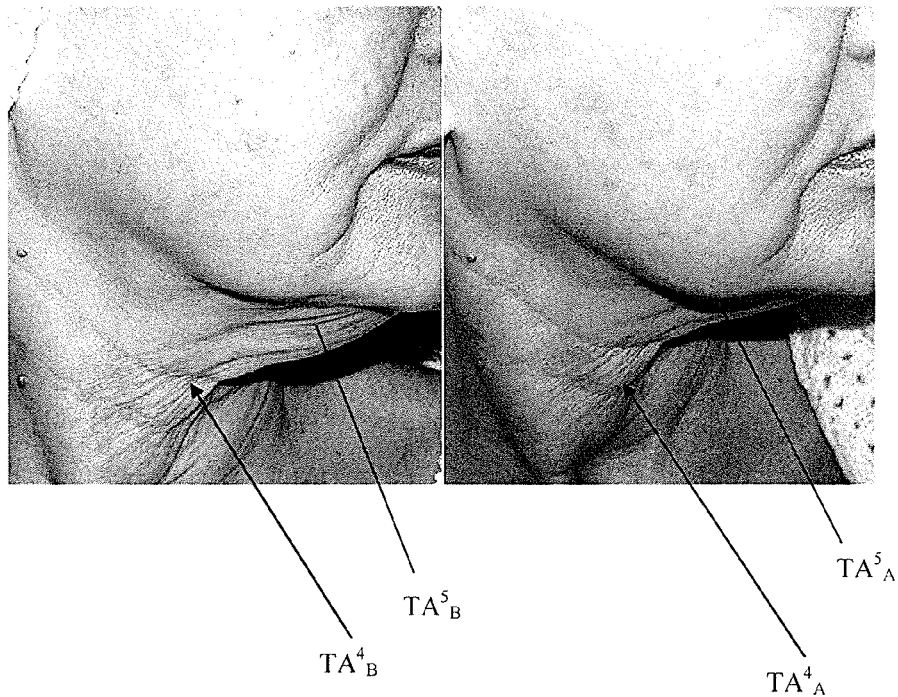
FIGS. 10A and 10B are before and after images of a patient treated according to another exemplary embodiment.

The images of FIGS. 9A, 9B, 10A, and 10B were taken with a Nikon digital camera Coolpix 995, fine resolution of 2048×1536 pixels and automatic adjusting enabled. The images of FIGS. 9A and 10A are pretreatment images and images of FIGS. 9B and 10B are post treatment images. Each after image was taken after 2 to 4 treatments, and specifically was taken immediately after finishing treatment. Where provided the subsequent images were taken 6 months to 1 year after final treatment without receiving any new treatment during that period.

In the illustrative embodiments as used to produce the results shown in FIGS. 9-10, the following equipment was utilized. A preoperative cooling gel having a temperature of between 2° C. to 6° C. was applied to the area being treated. In some cases, an anesthetic cream EMLA was also applied. As shown if FIGS. 8A, 8B, 8C, and 8D, the preoperative cooling gel 106 is applied directly to the skin surface of the treatment area TA before application of the radiation beam, and remains during application of the radiation beam. As shown in FIG. 8A, the vessels on the cheek of the patient are clarified for treatment. FIG. 8B illustrates a gel with light polarization that magnifies the underlying vessels to show details of area to be treated. FIG. 8C illustrate application prior to initial treatment while FIG. 8D illustrates a subsequent treatment after a passage of time from the initial treatments.

The radiation beam was generated using an IPL Quantum SR-HR available from Lumenis, Santa Clara Calif. and Yokenhamm, Israel. The radiation beam was filtered using two filters, a 560 nm filter and a 590 nm filter. The radiation beam was applied using a double pulse. The first pulse 1° pulse had a pulse width of 2.4 msec. There was then a delay of between 20 to 50 msec. The second pulse 2° pulse was then applied having a pulse width from 5 to 6 msec. The power of the radiation beam was set at between 22 to 26 joules/cm$^2$ G/cm$^2$). The IPL Quantum chiller was set at the medium setting.

In some tests, it was observed that the skin tightening can be improved with more comfort for the patient where lower powers, such as between 22 to 23 joules/cm$^2$, was used and where the delay was extended such as between 30 to 50 msec.

The total treatment for a given treatment area can range in the number of pulses in some cases but can vary based on the size of the area being treated at a particular treatment session. Typically, a full facial treatment can include 250 to 300 pulses and can last 40 minutes. Additionally, a post treatment moisturizing can be provided by application of a neutral cream, such as one having an SPF from 30 to 60.

In one controlled trial of one of the embodiments as described above, patients received from 3 to 5 full face treatments at intervals of 3 to 6 weeks. The skin tightening changes were registered at the end of the treatments and also from 6 to 18 months following the last treatment. It was observed, and registered and quantified with regard to face and neck skin tightening and contraction immediately after finishing the treatments and until 18 months after the first treatment. FIG. 9A illustrates a facial treatment of one patient wherein the cheek and the neck area were to be treated, such as indicated to three exemplary specific treatment areas $TA^1_B$, $TA^2_B$, and $TA^3_B$. FIG. 9B illustrates these same treatment areas $TA^1_A$, $TA^2_A$, and $TA^3_A$ following treatment. As can be seen, a substantial tightening of the skin in the cheek and neck has occurred especially in $TA^2_A$, and $TA^3_A$. FIG. 10A illustrates another example of a pretreatment loose skin condition in the neck with FIG. 10B illustrating the tightened neck skin following treatment, the before areas shown as $TA^4_B$, and $TA^5_B$, and the after areas shown as $TA^4_A$, and $TA^5_A$. As described herein, the use of IPL using a lower energy level than recommended by the manufacturer of the IPL system and therefore a lower energy level than is common in practice, is applied in multiple applications at the same treatment spot along with the chiller (IPL-QUANTUM) enables the placement of more temperature on the dermis without affecting the skin surface and thus making possible the formation of new collagen that tightens and contracts face and neck skin. Additionally, the more severe the photodamage of the initial skin, the more target tissue (melanin-hemoglobin) present before the initial treatment, and therefore the more temperature created in the dermis which results in a greater amount of tightening. As provided herein by several exemplary embodiments, an IPL (Intense Pulsed Light) technology using the lower energy level in multiple applications on the same treatment area along with the addition of preoperative and operative such as by contact cooling and/or cold gel (Dynamic cooling-Precooling), by ways of examples, a higher heat accumulation on the dermis can be achieved while still protecting the epidermis, thus not just improving at the pigment, vascular, pores diameter, and texture levels but also attaining skin contraction and tightening as a mediate effect after consecutive treatments.

The practicing of the present disclosure has found that the more photodamage present in the patient, the better the results that can be attained by the present methods, as the more target tissue present in the treatment area, there is an increase in the temperature in the dermis during treatment, resulting in more neocollagen being heated which in turn produces more tightening of the skin from the treatments.

After the skin was rearranged and tightened, an apparent slimming of round faces and thick necks occurred. Additionally, a filling effect on scarring depressions also occurred which was a result of the formation of neocollagen in the dermis. Such results have been shown in tests that continued months after completion of the treatments described herein, providing for increased temperature within the dermis while also providing protection of the epidermis during treatment through the described preoperative and operation coolings, nonablative tightening effects in the dermis are enhanced and the production of collagen is promoted.

As noted herein, any reference to a particular wavelength or value is not intended to be limited to that exact number but within a rounded or proximate value and the term "about" while often stated explicitly herein should also be implied in all such recitations and readings unless otherwise stated. When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A method for treatment of dermatological conditions of skin comprising:
    precooling a surface of the skin to below a normal temperature of the skin surface,
    wherein the precooling of the skin surface result in a temperature of the epidermis of about 0° C. and a temperature of the dermis of about 30° C.;
    applying a beam of radiation to the surface of the skin having a wavelength between about 515 nm to about 660 nm, a fluence less than about 26 j/cm², wherein the beam includes two or more pulses with each pulse having a pulse width and a pulse duration;
    applying dynamic cooling to the surface of the skin simultaneous with applying the beam of radiation to the surface of the skin, wherein the dynamic cooling maintains the temperature of the surface of the skin to an average increase of about 35° C. during the applying of the radiation beam; and
    applying a post treatment moisturizing cream to the surface of the skin after the applying of the radiation beam.

2. The method of claim 1, further comprising:
    repeating the precooling, applying the radiation beam and applying dynamic cooling at between about 3 and about 6 weeks following the first precooling, applying the radiation beam and applying the dynamic cooling.

3. The method of claim 2 wherein the precooling is a first precooling, the applying of a radiation beam is a first applying of a radiation beam and the applying dynamic cooling is a first applying of dynamic cooling, the combination of which is a first treatment, further comprising the steps of:
    applying a second treatment after a predefined period of time following the first treatment that includes the first precooling, the first treatment of applying the radiation beam and the first treatment of applying the dynamic cooling, the second treatment including applying a second precooling of the surface of the skin, applying a second beam of radiation to the surface of the skin, and applying a second dynamic cooling to the surface of the skin simultaneous with applying the second beam of radiation.

4. The method of claim 3 wherein applying the radiation beam includes applying the beam having two wavelength bands, a first band between about 515 nm to about 590 nm and a second band between about 550 nm to about 660 nm, and wherein a first treatment applies a radiation beam of the first band and the second treatment applies a radiation of the second band.

5. The method of claim 1 wherein applying the radiation beam includes filtering the radiation beam using at least one cut-off filter.

6. The method of claim 5 wherein at least one of two cut-off filters are utilized, a first at about 560 nm and a second at about 590 nm.

7. The method of claim 1 wherein applying the radiation beam includes applying three or more pulses of radiation.

8. The method of claim 1 wherein a first pulse is a 1 degree pulse having a duration of about 2.4 msec and a second pulse is a 2 degree pulse having a duration of about 5 msec to about 6 msec.

9. The method of claim 1 wherein each pulse is delayed from another pulse by about 20 to about 50 msec.

10. The method of claim 1 wherein a second pulse is delayed from a first pulse by about 30 to about 50 msec and wherein applying the radiation beam includes applying the beam having a power of between about 22 j/cm² to about 26 j/cm².

11. The method of claim 1 wherein applying the radiation beam is applying a plurality of pulses, each pulse having a pulse width, and a pulse duration, wherein each pulse is spaced apart from another one of the pulses.

12. The method of claim 11 wherein each pulse has the same pulse width.

13. The method of claim 1 wherein applying the radiation beam includes applying the beam having a power in the range of at least one of between about 15 j/cm² and about 25 j/cm² and between about 22 j/cm² and about 26 j/cm².

14. The method of claim 1 wherein applying the post treatment moisturizing neutral cream to the surface of the skin applying a neutral cream having a sun protection factor (SPF) from about 30 to about 60.

15. The method of claim 1 wherein precooling the surface of the skin includes applying a cooling substance to the skin having a temperature of between about −8° C. and about 2° C.

16. The method of claim 1 wherein applying the applying dynamic skin cooling includes cooling the skin by more than about 10° C. during applying the radiation beam.

17. The method of claim 1 wherein applying the radiation beam includes using an intense pulsed light (IPL) system wherein applying dynamic cooling includes using an IPL-Quantum system as the IPL.

18. The method of claim 17 wherein the dynamic coolings of the skin during the applications of the radiation cools the epidermis to 35 and the dermis to 65° C.

19. The method of claim 1 wherein applying dynamic cooling includes applying a cryogen spray to the surface of the skin during applying the radiation beam.

20. The method of claim 1 wherein the steps of dynamic cooling of the skin during the applying of the radiation is cooling the epidermis to 35° C. and the dermis to 65° C.

21. A method for treatment of dermatological conditions of skin comprising:
    precooling a surface of the skin for a first treatment to below a normal temperature of the skin surface, wherein the precooling of the skin surface result in a temperature of the epidermis of about 0° C. and a temperature of the dermis of about 30° C.;

applying a first beam of radiation to each of a plurality of treatment areas of the surface of the skin, the first beam having a wavelength between about 560 nm to about 660 nm and a fluence less than about 26 j/cm$^2$ and wherein the beam includes a first pulse and a second pulse applied to each treatment area;

applying a first dynamic cooling to the surface of the skin simultaneous with applying the beam of radiation, wherein the dynamic cooling maintains the temperature of the surface of the skin to an average increase of about 35° C. during the applying of the radiation beam;

precooling a surface of the skin for a second treatment to below a normal temperature of the skin surface, the second treatment following the first treatment by a predefined period of time exceeding one week;

applying a second beam of radiation to each of the treatment areas, the second beam having a wavelength between about 590 nm and about 660 nm and a fluence less than about 26 j/cm$^2$ and wherein the beam includes a first pulse and a second pulse applied to each treatment area;

applying a second dynamic cooling to the surface of the skin simultaneous with applying the second beam of radiation, wherein the dynamic cooling maintains the temperature of the surface of the skin to an average increase of about 35° C. during the applying of the radiation beam;

applying a post treatment moisturizing neutral cream to the surface of the skin after each applying of the radiation beams.

22. The method of claim 21, wherein the steps of the first treatment with the first beam are repeated two to three times before the steps of the second treatment with the second beam.

* * * * *